United States Patent [19]
Saito et al.

[11] Patent Number: 4,908,119
[45] Date of Patent: Mar. 13, 1990

[54] APPARATUS FOR DETERMINING OXYGEN CONCENTRATION

[75] Inventors: Toshitaka Saito, Toyohashi; Hiromi Sano; Soji Ota, both of Nagoya; Syohei Udo, Anjo, all of Japan

[73] Assignee: Nippondenso Co., Ltd., Kariva, Japan

[21] Appl. No.: 91,964

[22] Filed: Sep. 1, 1987

[30] Foreign Application Priority Data

Sep. 1, 1986 [JP] Japan .................. 61-205311
May 19, 1987 [JP] Japan .................. 61-122031

[51] Int. Cl.⁴ .................................. G01N 27/46
[52] U.S. Cl. .................. 204/426; 204/427; 204/429
[58] Field of Search .................. 204/15, 421–429

[56] References Cited

U.S. PATENT DOCUMENTS

| | | | |
|---|---|---|---|
| 3,879,279 | 4/1975 | Baucke | 204/419 |
| 4,119,513 | 10/1978 | Shum et al. | 204/426 |
| 4,155,828 | 5/1979 | Takao et al. | 204/426 |
| 4,157,282 | 6/1979 | Riddel | 204/426 |
| 4,172,247 | 10/1979 | Ikeura | 204/427 |
| 4,242,303 | 12/1980 | Takahashi et al. | 422/98 |
| 4,264,425 | 4/1981 | Kimura et al. | 204/425 |
| 4,282,080 | 8/1981 | Muller et al. | 204/426 |
| 4,283,261 | 8/1981 | Maurer et al. | 204/426 |
| 4,428,817 | 1/1984 | Isenberg | 204/427 |
| 4,450,065 | 5/1984 | Yamada et al. | 204/426 |
| 4,574,042 | 3/1986 | Shirashi | 204/426 |
| 4,642,174 | 2/1987 | Shibata | 204/424 |
| 4,659,448 | 4/1987 | Gordon | 204/428 |

FOREIGN PATENT DOCUMENTS 54-98298   8/1979  Japan.
55-116248  9/1980  Japan.
61-272649  2/1986  Japan.

Primary Examiner—T. Tung
Attorney, Agent, or Firm—Cushman, Darby & Cushman

[57] ABSTRACT

Outer air serving as a reference gas for determining oxygen concentration is guided to a hollow portion of a core. The core is formed in an insulating cylinder whose distal end is closed and whose proximal end is open to receive the reference gas. An opening is formed on the outer surface of the core, to communicate with the hollow portion. An oxygen concentration sensor element made of a solid-state electrolyte layer having first and second electrode layers one on each surface thereof is mounted such that it closes the opening. A sheet member made of an insulating sheet is wound around the sensor element mounted on the sensor element, and is fixed thereon. A window is formed in the sheet so as to expose the surface of the sensor element. A heater is formed around the window. Wiring layers respectively connected to both terminals of the heater are formed on the sheet. Wiring layers adapted to contact the first and second electrode layers of the sensor element are also formed on the sheet. The four wiring layers are respectively guided to grooves formed in the outer surface of the proximal end of the core. A protective layer in the form of a porous insulator is formed on the outer surface of the sheet member.

10 Claims, 8 Drawing Sheets

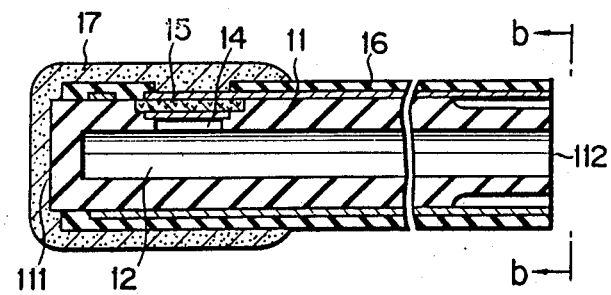
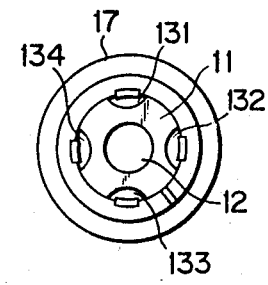
F I G. 1A    F I G. 1B
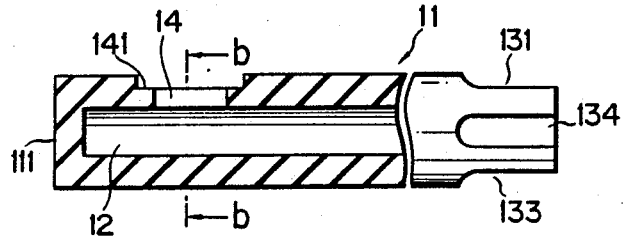
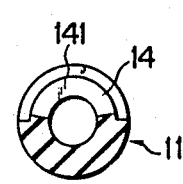
F I G. 2A    F I G. 2B
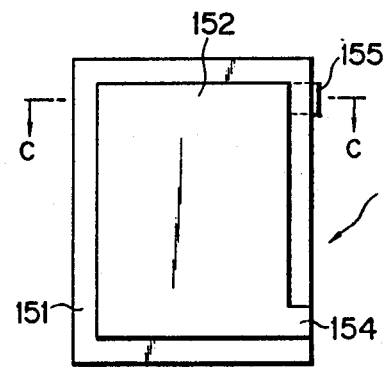
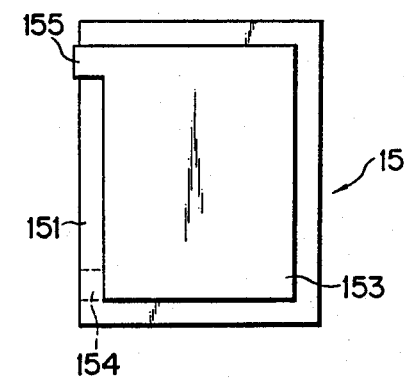
F I G. 3A    F I G. 3B
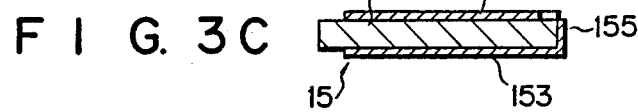
F I G. 3C

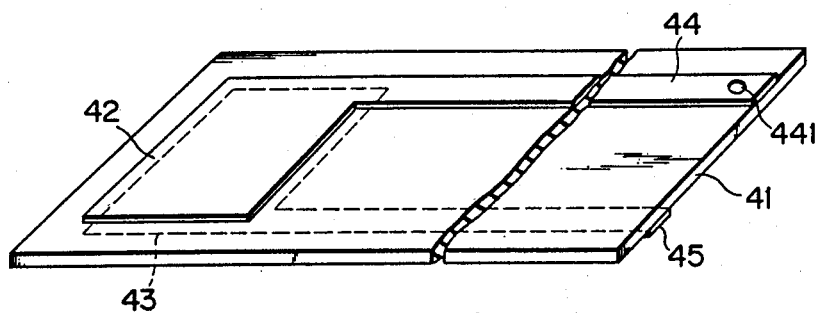
F I G. 6A
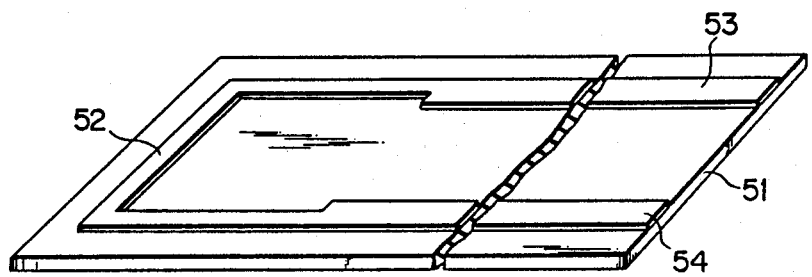
F I G. 6B
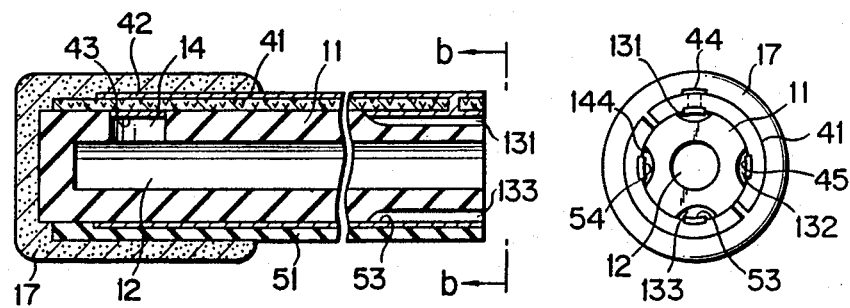
F I G. 7A        F I G. 7B

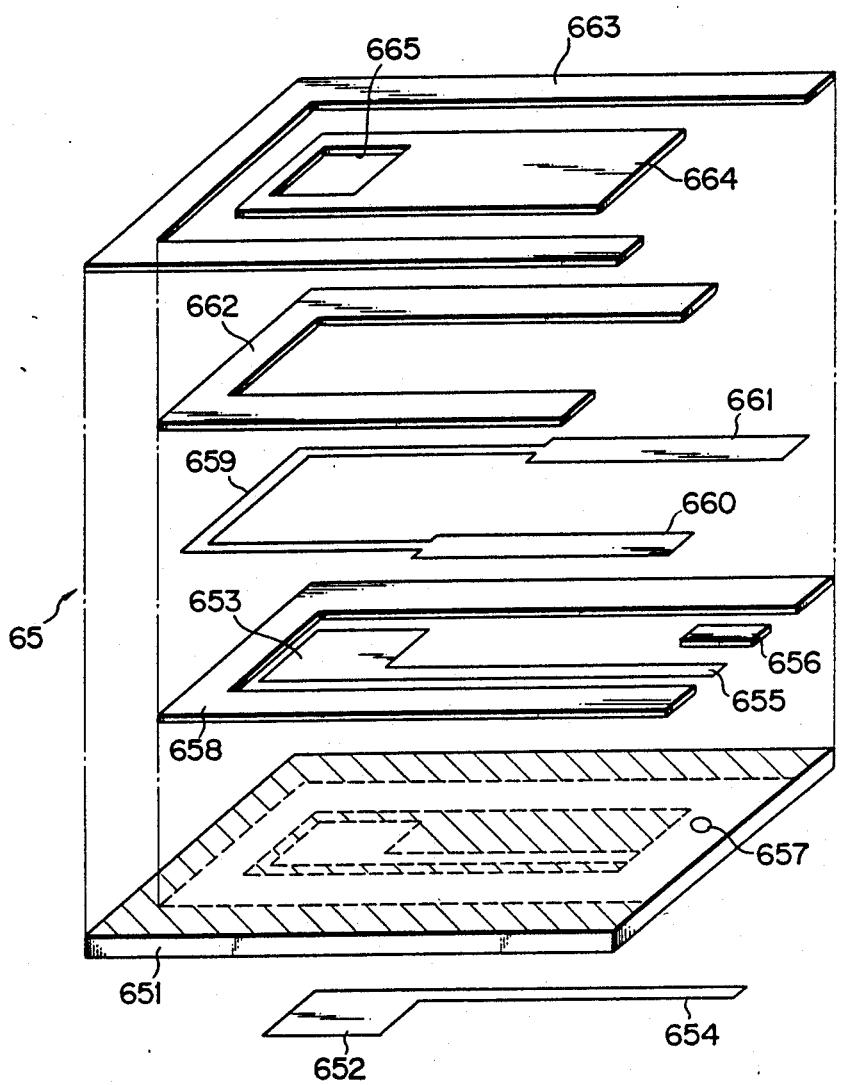
F I G. 10

APPARATUS FOR DETERMINING OXYGEN CONCENTRATION

BACKGROUND OF THE INVENTION

The present invention relates to an apparatus for determining oxygen concentration, which measures the amount of oxygen contained in the exhaust gas of, for example, an internal combustion engine, so as to control the fuel to be injected into the engine.

In order to determine, for example, the optimum amount of fuel to be injected into an internal combustion engine, air/fuel ratio control is performed to measure the amount of oxygen contained in the exhaust gas, whereby the air/fuel ratio in a combustion chamber can then be set to an optimal value.

In order to perform air/fuel ratio control, an oxygen concentration sensor is positioned in the exhaust manifold of the engine, so as to measure the amount of oxygen contained in the exhaust gas flowing therethrough, whereupon the fuel injection quantity is then corrected and re-calculated on the basis of a signal from the oxygen concentration sensor. The fuel to be injected into the engine is calculated on the basis of engine speed, the volume of intake air, and the like.

A conventional oxygen concentration detection apparatus comprises a sensor element which is constituted by a solid-state electrolyte material of a $ZrO_2$-based oxygen ionic conductor doped with $Y_2O_3$, $Yb_2O_3$, or the like. For example, a cup-like sensor element with a closed cylindrical bottom portion is constituted by a solid-state electrolyte material, on the inner and outer surfaces of which electrode layers are formed. The electrolyte material is exposed in an atmosphere of a gas being subjected to measurement, while at the same time, outer air as a reference gas is supplied to the interior thereof. The electrolyte material is then heated by a heater so as to accurately measure the oxygen concentration.

Since, in a conventional oxygen concentration determining apparatus, the cup-like sensor portion must be formed of solid-state electrolyte material, the fabrication process is therefore complicated. In addition, since it has a cup-like shape, it is difficult to increase the mechanical strength of the sensor portion. Therefore, when the cup-like sensor portion is attached to an internal combustion engine portion and subjected to vibration, many countermeasures must be taken. The structure of the heater is also complicated.

A sensor element as described in U.S. Pat. No. 4,282,080 has been proposed, with the aim of solving the above problems. The oxygen concentration sensor element described in this patent has a two-layered (a heater layer and an electrode layer) structure formed on each major surface of a solid-state electrolyte plate, to thereby constitute an integral structure. An outer air inlet opening is formed in a portion corresponding to one major surface of the sensor element of the solid-state electrolyte plate on which the heater and the electrode are integrally formed.

The laminated sensor element which surrounds the outer air inlet port is basically plate-like in shape. Therefore, the position of the element with respect to the direction of the gas flow inevitably adversely influences the accuracy of determining the oxygen concentration.

Since the element is plate-like in shape, it is difficult to obtain a sufficiently high mechanical strength. Since the electrode layers are formed on both surfaces of the solid-state electrolyte plate and the heaters are formed thereon, a plurality of insulating layers are required to electrically insulate the electrode layers from the heaters. As a result, the structure of the sensor element is complicated.

Another conventional oxygen concentration sensor is proposed in Japanese Patent Disclosure (Kokai) No. 61-272649. In this sensor, a plurality of grooves are formed on the outer surface of a rod-like core made of an electrically insulating material such as $Ae_2O_3$. These grooves are used as channels for guiding outer air as a reference gas. An inner electrode, an outer electrode, and a heater are formed on each major surface of a solid-state electrolyte sheet. This solid-state electrolytic sheet is then wound around the outer surface of the core.

In the oxygen sensor having the structure described above, the grooves are formed to guide outer air as a reference gas. If the sensor is designed such that the volume of the core decreases so as to reduce, for example, the heat capacity, the groove cannot be as wide or deep as is desired. Since the width and/or depth of the groove is limited, it is difficult to smoothly guide outer air to a portion of the solid-state electrolyte layer, and to determine with accuracy the oxygen concentration in, for example, engine exhaust gas.

SUMMARY OF THE INVENTION

It is an object of the present invention to provide an oxygen concentration determining apparatus having sufficiently high mechanical strength that when the amount of oxygen contained in an exhaust gas generated by an internal combustion engine is to be measured, it can withstand the high level of mechanical vibration generated thereby.

It is another object of the present invention to provide an oxygen concentration determining apparatus which has a simple mechanical structure, no directivity with respect to the flow of the gas to be measured, and a wide path for guiding outer air as a reference gas, and which allows easy measurement of oxygen concentration with high precision.

It is a further object of the present invention to provide an oxygen concentration determining apparatus which effectively absorbs stress upon heating and expansion of a solid-state electrolyte material constituting a sensor element, thereby preventing damage to the apparatus, and which can be effectively used as an oxygen concentration sensor in an exhaust gas from, for example, an automobile engine.

In an oxygen concentration detection apparatus according to the present invention, an insulator is used to form a cylindrical core whose distal end is closed. An opening is formed at a side wall near the distal end of the core and communicates with a hollow portion of the core. A solid-state electrolyte layer having electrode layers on both its surfaces is located such that it closes the opening. The electrode layer formed on one major surface of the solid-state electrolyte layer opposes the hollow portion of the core to which a reference gas is supplied, through the opening.

In the oxygen concentration detection apparatus having the structure described above, the hollow portion formed inside the core communicates with the outer air, and one major surface of the electrolyte layer is exposed to the reference gas atmosphere of outer air, while the other major surface is exposed to an atmosphere of a gas to be measured. Therefore, an electrical signal proportional to the amount of oxygen contained in the gas to be measured can be obtained. In this case, the electrodes respectively formed on both the surfaces of the solid-state electrolyte layer can be easily connected externally by conductor wirings, if the conductor wiring is formed on a proper insulator sheet or around the surface of the core, to constitute the solid-state electrolyte layer. In this case, conductor wiring layers, heaters, and the like can be simultaneously and easily formed.

In such an oxygen concentration detection apparatus, the solid-state electrolyte layer can be formed by using the core as a basic element. The reference gas atmosphere can be provided in the hollow portion of the core. The amount of intake reference gas can be properly supplied, and high-precision measurement can be easily performed. The overall structure can be simple, using the core as a basic element. The assembly structure for, for example, an exhaust manifold can easily be simplified and have sufficiently high mechanical strength. In this case, the position of the core with respect to the direction of gas flow has no influence on the accuracy of determining the oxygen concentration.

BRIEF DESCRIPTION OF THE DRAWINGS

FIG. 1A is a sectional view of an oxygen concentration detection apparatus according to an embodiment of the present invention;

FIG. 1B is a view of the apparatus thereof taken along the line b—b of FIG. 1A;

FIG. 2A is a partially cutaway side view of a core constituting the detection apparatus;

FIG. 2B is a side view of a portion corresponding to the line b—b of FIG. 2A;

FIGS. 3A to 3C are views showing a sensor element of a solid-state electrolyte layer used in the detection apparatus, in which FIGS. 3A and 3B are plan views showing both major surfaces of the element, and FIG. 3C is a sectional view thereof taken along the line c—c of FIG. 3A;

FIGS. 6A and 6B are views showing a solid-state electrolytic layer and an insulating sheet, both of which are used in a detection apparatus according to a second embodiment of the present invention;

FIG. 7A is a sectional view of the detection apparatus according to the second embodiment;

FIG. 7B is a view of the detection apparatus thereof taken along the line b—b of FIG. 7A;

FIG. 10 is an exploded view of a sensor element portion constituting the third embodiment;

DETAILED DESCRIPTION OF THE PREFERRED EMBODIMENTS

Figure 4:
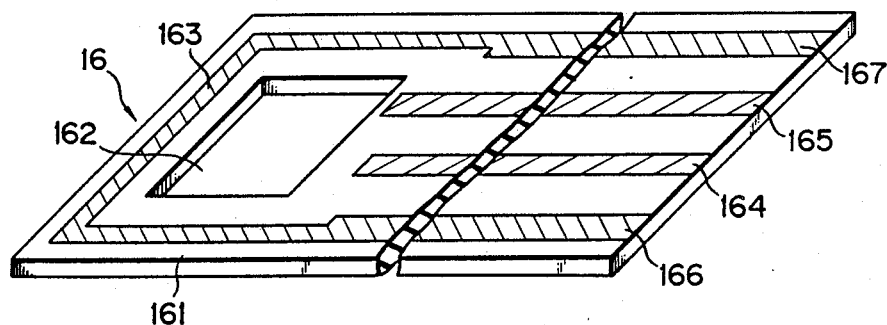
FIG. 4 is a perspective view of an insulating sheet constituting the sensor element.

FIGS. 1A and 1B show a structure of a detection mechanism portion of an oxygen concentration detection apparatus. The mechanism portion comprises cylindrical core 11. Core 11 is made of an electrical insulator such as $Ae_2O_3$ or $Si_3N_4$. As shown in FIG. 2, distal end 111 is closed, and an opening is formed at proximal end 112. The opening of proximal end 112 communicates with outer air (not shown). A reference outer air atmosphere is set in hollow portion 12 of core 11. Four grooves 131 to 134 are formed on the outer surface of proximal end 112 portion of core 11 so as to constitute terminals. Grooves 131 to 134 are parallel to the axis of core 11.

Opening 14 is formed on the outer surface of core 11 to communicate with hollow portion 12 at a position near the distal end. Holding portion 141 is formed by a step at a portion around opening 14. Oxygen concentration sensor element 15 is fitted in opening 14 and held in position by means of step 141.

FIG. 3 is an enlarged view of oxygen concentration sensor element 15. Sensor element 15 is plate-like solid-state electrolyte layer 151. Electrolyte layer 151 is made of a $ZrO_2$ (zirconium oxide) oxygen ionic conductor material doped with $Y_2O_3$, $Yb_2O_3$, or the like. Electrolyte layer 151 is fitted along the arcuated surface of opening 14.

First and second electrode layers 152 and 153 are respectively formed on major surfaces of solid-state electrolyte layer 151 by deposition or printing. Lead electrodes 154 and 155 respectively extend from electrode layers 152 and 153 toward corresponding edges.

Electrode layers 152 and 153 are porous electrodes made of platinum or the like. Oxygen contained in gases present on the electrode surfaces is guided to solid-state electrolyte layer 151. In other words, oxygen concentration sensor element 15 serves as an electrochemical cell whose current level is determined by the concentration of oxygen.

Sheet member 16 is wound around core 11 while oxygen concentration sensor element 15 is fitted in opening 14. FIG. 4 shows only sheet member 16. Sheet member 16 is constituted such that sheet 161 of the same material as that of core 11 is used as a body.

Window 162 having the same size as that of opening 14 is formed at a position of core 11 corresponding to opening 14. Heater 163 is formed by a Pt or W thin film so as to surround window 162. Pt or W wiring layers 164 and 165 serving as first and second lead wires are formed to extend from the window 162 portion toward proximal end 112 of core 11. Wiring layers 164 and 165 are guided to grooves 131 and 132 formed in core 11 while sheet member 16 is wound around core 11. Wiring layers 164 and 165 are exposed in grooves 131 and 132, respectively.

Oxygen concentration sensor element 15 is fitted in opening 14 of core 11, and sheet member 16 is wound around core 11 such that a sheet member surface having heater 163 and the like faces inside. In this state, sensor element 15 is fixed and held to holding portion 141 around opening 14 by sheet member 16. In this case, wiring layers 164 and 165 are respectively brought into contact with lead electrodes 154 and 155 of sensor element 15.

In this case, first electrode layer 152 of oxygen concentration sensor element 15 opposes window 162 of sheet member 16, and first electrode layer 152 is exposed outside.

Wiring layers 166 and 167 serving as lead wires from heater 162 are formed on sheet 161 and are respectively parallel to wiring layers 164 and 165 and guided to grooves 133 and 134 of core 11.

The oxygen concentration detection mechanism is fabricated as follows. Core 11 is prepared by molding a predetermined material, and oxygen concentration sensor element 15 including solid-state electrolyte layer 151 having electrode layers and the like formed by screen printing thereon is prepared. Sensor element 15 is fitted in opening 14. Sheet member 16 having heater 163 and wiring layers 164 to 167, both of which are formed by screen printing or the like, is wound around the outer surface of core 11 such that window 162 coincides with the position of opening 14. The resultant structure is baked. Thereafter, a ceramic coating layer of $Ae_2O_3$ or $MgO \cdot Ae_2O_3$ spinnel is formed porous protective layer 17 for protecting electrodes and the like according to plasma spray welding or the like.

The porosity of the ceramic coating layer as protective layer 17 can be freely adjusted. By adjusting the porosity, the sensor can be selectively used as a potentiometric or polarographic sensor.

Figure 5:
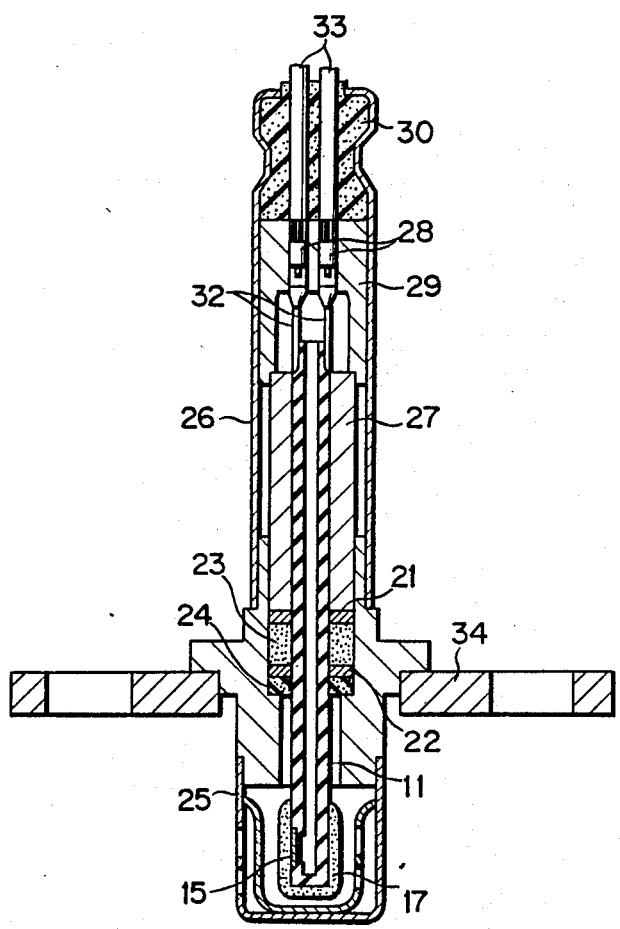
FIG. 5 is a sectional view for explaining a structure of an exhaust gas detection sensor constituted by using the sensor element.

FIG. 5 show a structure of an oxygen concentration sensor using the oxygen concentration detection mechanism having the above structure. A cylindrical detection mechanism constituted by suing core 11 as the main element is set in a hollow portion formed in the central portion of housing 20. The cylindrical detection mechanism is held in the hollow portion of housing 20 by rings 21 and 22, talc 23, and packing 24. The distal and proximal end portions of the detection mechanism can be separated from each other by packing 24 in housing 20.

THe detection mechanism distal end portion having oxygen concentration sensor element 15 therein extends from housing 20. Cover element 25 which covers the portion corresponding to extended sensor element 15 is mounted in housing 20. A large number of through holes are formed in cover element 25. A gas to be measured enters the distal end sensor element 15 portion of the detection mechanism through these through holes and is brought into contact with sensor element 15 through protective layer 17.

Cylindrical cover protection 26 is brazed to housing 20 at a position opposite to cover element 25. The axis of cover protection 26 is aligned with core 11 of the oxygen concentration detection mechanism. Holder 27 is interposed between core 11 and cover protection 26 to fix core 11.

Lead connection 28 is formed in insulator 29 coaxial with holder 27 in cover protection 26. The position of insulator 29 is fixed by rubber bushing 30. In this case, insulator 29 and rubber bushing 30 are designed to have air permeability. Outer air is guided to the opening of the proximal portion of core 11 through rubber bushing 30 and insulator 29. Therefore, the reference gas atmosphere using outer air is set in the hollow portion of core 11.

Lead wires 32 are connected to lead connection 28. Wires 32 are also connected to wiring layers 164 and 165 from the sensor element and wiring layers 166 and 167 from the heater in grooves 131 to 134 formed in the proximal portion of core 11. Lead connection is externally guided via wire leads 33 extending through rubber bushing 30.

The oxygen concentration detection apparatus is mounted in the exhaust manifold by frame 34 while the apparatus extends through the exhaust manifold of the internal combustion engine. The portion of oxygen concentration sensor element 15 is set in the exhaust gas. The outer surface of solid-state electrolyte layer 151 is brought into contact with a gas subjected to measurement, i.e., an exhaust gas, through first electrode layer 152 and protective layer 17. In this case, the inner surface of solid-state electrolyte layer 151 is in contact with the reference gas atmosphere of the hollow portion of core 11 through second electrode layer 153.

A current corresponding to an amount of oxygen contained in the exhaust gas flows between first and second electrode layers 152 and 153 respectively formed on both surfaces of solid-state electrolyte layer 151 flows. In this case, solid-state electrolyte layer 151 is heated by heater 163, and high-precision oxygen concentration detection can be performed.

FIGS. 6 and 7 show a second embodiment of the present invention. As shown in FIG. 6A, oxygen concentration sensor element 15 is constituted by solid-state electrolyte layer 41 formed to surround core 11 by ½ the circumferential length of core 11. First and second electrode layers 42 and 43 are respectively formed on both surfaces of solid-state electrolyte layer 41 at a position corresponding to opening 14 of core 11. Wiring layers 44 and 45 are printed to extend from electrodes 42 and 43 toward the proximal portion of core 11. In this case, wiring layer 44 is guided toward the inner surface side of solid-state electrolyte layer 41 via through hole 441.

Sheet 51 shown in FIG. 6B is wound around core 11 for the remaining half of the circumferential length. Sheet 51 is made of the same insulating material as that of core 11. Heater 52 and wiring layers 53 and 54 are formed on the surface of sheet 51.

Solid-state electrolytic layer 41 shown in FIG. 6A and sheet 51 are wound around core 11 by halves of the circumferential length, as shown in FIG. 7. The resultant structure is baked.

Figures 8A, 8B:
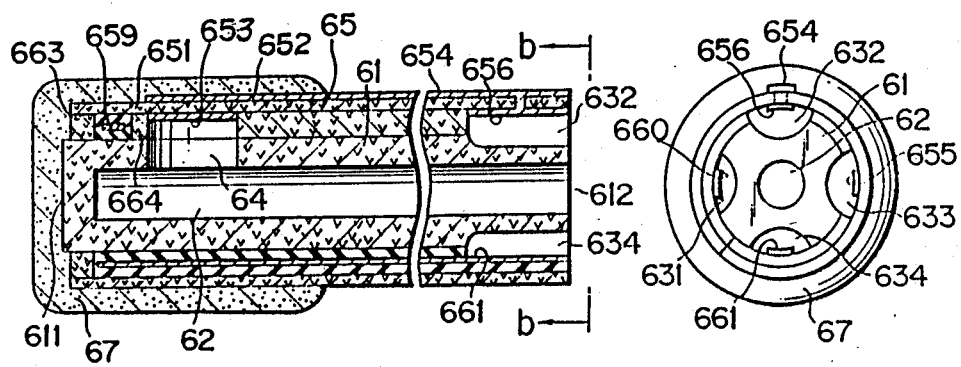
FIG. 8A is a sectional view for explaining a third embodiment of the present invention.
FIG. 8B is a view thereof taken along the line b—b of FIG. 8A.
Figure 9A:
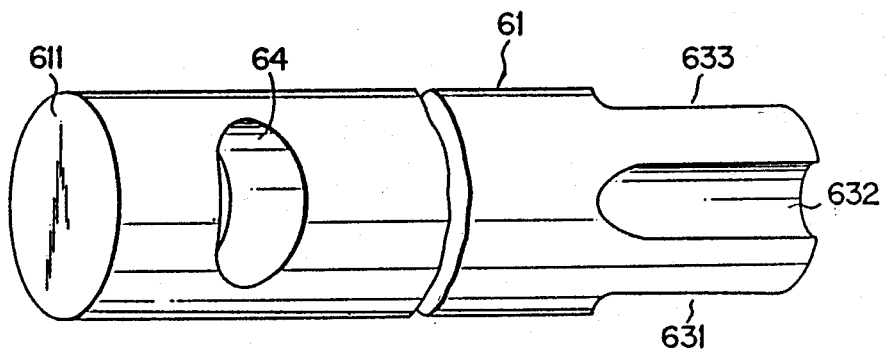
FIGS. 9A and 9B are respectively a perspective view and a partially cutaway side view of a core used in each embodiment.
Figure 9B:
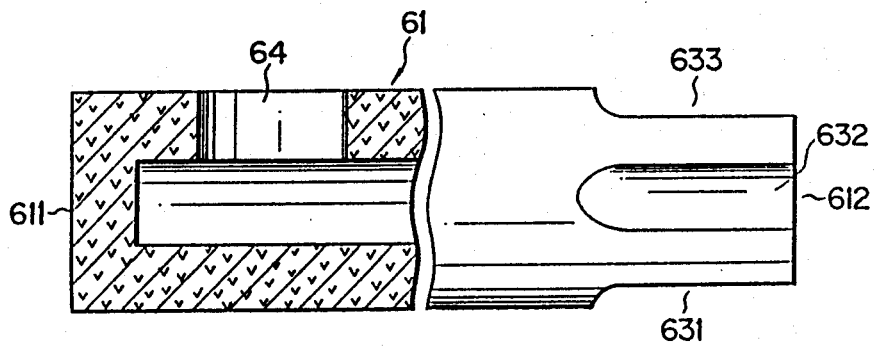

FIG. 8 shows a third embodiment. Core 61 having closed distal end 611 is made of an oxygen ionic conductor material prepared by solid-dissolving 95 mol % of $ZrO_2$ and 5 mol % of $Y_2O_3$. Core 61 has hollow portion 62 with open proximal end 612, as shown in FIGS. 9A and 9B. Four grooves 631 to 534 are formed on the outer surface at proximal end 612. Opening 64 extending in hollow portion 62 is formed in the outer surface of core 61 at a position near the distal end. Oxygen concentration sensor element 65 is wound around the outer surface of core 61.

FIG. 10 is an exploded view of oxygen concentration sensor element 65. Sensor element 65 comprises solid-state electrolyte layer 651. Electrolyte layer 651 is formed into a plate of the same oxygen ionic conductor material as that of core 11 and has a size enough to cover the entire circumferential surface of core 61.

First and second electrode layers 652 and 653 are respectively formed by deposition or printing on both surfaces of plate-like solid-state electrolyte layer 651 at positions corresponding opening 64 of core 61. Wiring layers 654 and 655 are respectively formed on electrode layers 652 and 653. Wiring layers 654 and 655 are directed toward the proximal end of core 61. The distal end portions of wiring layers 654 and 655 are located at positions of grooves 632 and 633 while sensor element 65 is wound around core 61. The distal end portion of wiring layer 655 corresponding to second electrode 653 opposes groove 633. Wiring layer 656 is formed on solid-state electrolytic layer 651 at a position corresponding to groove 632. Wiring layer 656 is electrically connected to wiring layer 654 via through hole 657 formed in solid-state electrolyte layer 651.

First and second electrode layers 652 and 653 are formed as platinum porous electrodes containing a small amount of $ZrO_2$ oxygen ionic conductor material constituting solid-state electrolyte layer 651. Oxygen contained in gases present on the surfaces of electrode layers 652 and 653 is guided to the surface of solid-state electrolyte layer 651.

Insulating layer 658 of an $Ae_2O_3$ film which surrounds the region corresponding to second electrode layer 653 is formed on the surface of solid-state electrolyte layer 651 in which second electrode layer 652 is formed. Insulating layer 658 is formed to have a pair of legs respectively extending to grooves 631 and 634. Heater 659 of a Pt or W thin film mixed with $Ae_2O_3$ is formed on insulating layer 658. Wiring layers 660 and 661 are formed to extend along the pair of legs from both ends of heater 659. Wiring layers 660 and 661 respectively oppose grooves 631 and 634.

Insulating layer 662 of an $Ae_2O_3$ thin film is formed on insulating layer 658 on which heater 659 and the like are formed. In this case, insulating layer 662 is formed except for the distal end portions of wiring layers 660 and 661, so that the distal end portions of wiring layers 660 and 661 are exposed in grooves 631 and 634, respectively. A portion associated with heater 659 is electrically insulated from solid-state electrolyte layer 651 by insulating layers 658 and 662.

When the electrodes and heater are formed as described above, filling layers 663 and 664 are formed in a region (the region on solid-state electrolyte layer 651, as indicated by the hatched line) excluding the region in which insulating layer 658 for holding second electrode layer 653 and heater 659 is present. The thickness of each of filling layers 663 and 664 is the same as that of a sum of heater 659 and one of insulating layers 658 and 659. Filling layers 663 and 664 are made of the same oxygen ionic conductor material as that of solid-state electrolyte layer 651 and core 61. Window 665 corresponding to electrode layer 653 formed in filling layer 664 is formed at a position corresponding to opening 64 of core 61. Second electrode layer 653 opposes hollow portion 62 of core 61 through window 665 and is brought into contact with the reference gas atmosphere in hollow portion 62.

Figure 11A:
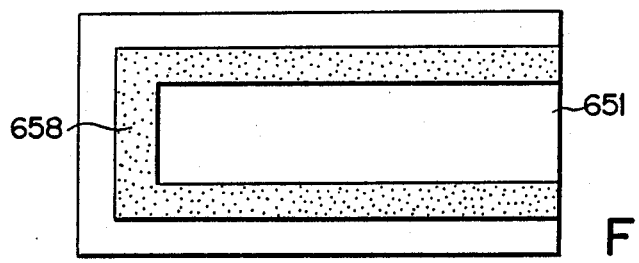
FIGS. 11A to 11D are sectional views for explaining the steps in manufacturing the sensor element.
Figure 11B:
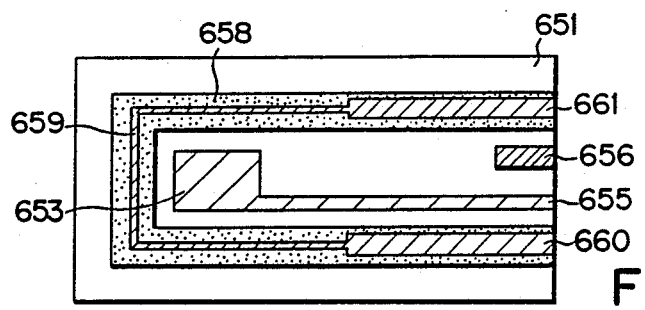
Figure 11C:
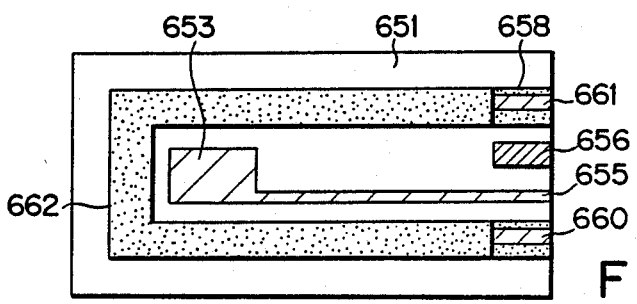
Figure 11D:
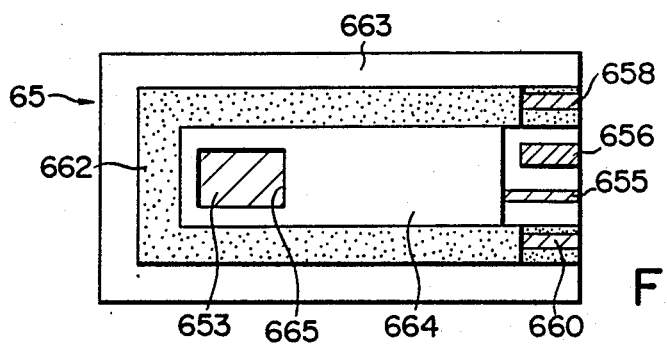

FIGS. 11A to 11D show steps in manufacturing oxygen concentration sensor element 65 described above. As shown in FIG. 11A, insulating layer 658 is formed on molded solid-state electrolyte layer 651 having a predetermined shape. As shown in FIG. 11B, second electrode layer 653 and wiring layers 655 and 656 are formed between the pair of legs of insulating layer 658 according to deposition or printing. Similarly, heater 659 and wiring layers 660 and 661 are formed on insulating layer 658. As shown in FIG. 11C, insulating layer 662 is formed on insulating layer 658 on which heater 659 is formed. As shown in FIG. 11D, filling layers 663 and 664 are formed on insulating layer 662, thereby preparing oxygen concentration sensor element 65. Although omitted in FIG. 11D, first electrode layer 652 is formed together with wiring layer 654 on the lower surface of solid-state electrolyte layer 651 according to deposition or printing.

Figure 12:
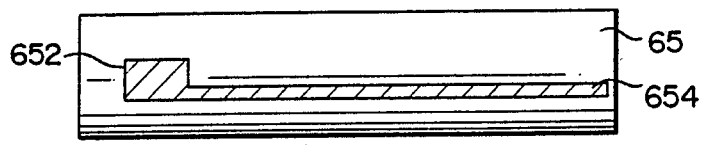
FIG. 12 is a view showing an outer appearance when the sensor element is mounted on a core.

FIG. 12 shows a state wherein oxygen concentration sensor element 65 thus prepared is wound around core 61. First electrode layer 652 and wiring layer 654 connected thereto are present on the outer surface of core 61. The resultant structure is baked while oxygen concentration sensor element 65 including the solid-state electrolyte material is wound around core 61. By baking, oxygen concentration sensor element 65 including solid-state electrolyte layer 651 is integrally bonded to core 61 through filling layers 663 and 664.

In this case, core 61, solid-state electrolyte layer 651, and filling layers 663 and 664 are made of the same material and have an identical expansion coefficient. Even if a large amount of heat is applied to these elements, no cracks occur, and thus a hermetic integral structure can be assured.

After baking, porous protective layer 67 of a ceramic coating layer is formed by plasma spray welding on the outer surface of the distal end portion of core 61 so as to cover first electrode layer 652 of oxygen concentration sensor element 65.

Figure 13A:
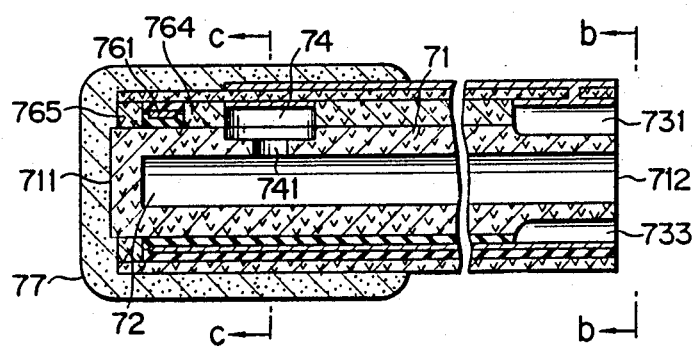
FIG. 13A is a sectional view of a detection apparatus of a fourth embodiment.
Figure 13B:
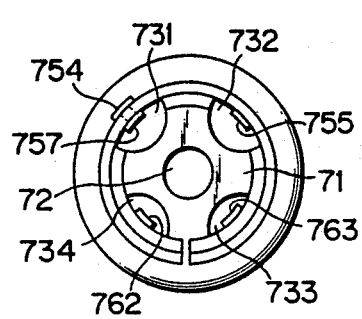
FIGS. 13B and 13C are respectively a view of the detection apparatus thereof takes alone the lines b—b and c—c of FIG. 13A.
Figure 13C:
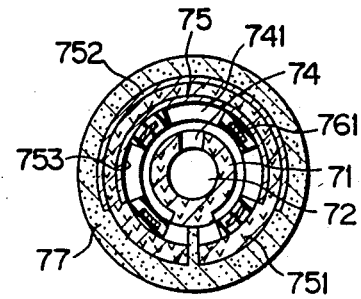

FIGS. 13A to 13C show a fourth embodiment of the present invention. Core 71 of this embodiment is made of the same oxygen ionic conductor material as that of the core of the third embodiment. Distal end 711 of core 71 is closed, and proximal portion 712 thereof is open. The opening communicates with outer air (not shown), and a reference gas atmosphere is set in hollow portion 72. Four grooves 731 to 734 are formed on the outer surface of proximal end 712 of core 71. Opening 73 communicating with hollow portion 72 is formed on the outer surface near the distal end of core 71.

Figure 14A:
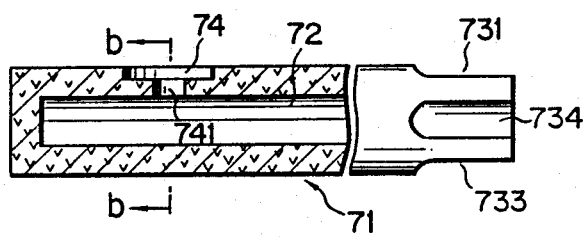
FIG. 14A is a partially cutaway side view of the core used in the above embodiment.
Figure 14B:
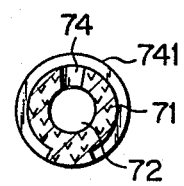
FIG. 14B is a sectional view of the portion corresponding to the line b—b of FIG. 14A.

FIGS. 14A and 14B show core 71. Opening 73 extends through hollow portion 72 by groove 741 formed by at least ¾ the circumferential length of core 71. Oxygen concentration sensor element 75 is wound and fixed on the outer surface of core 71.

Figure 15:
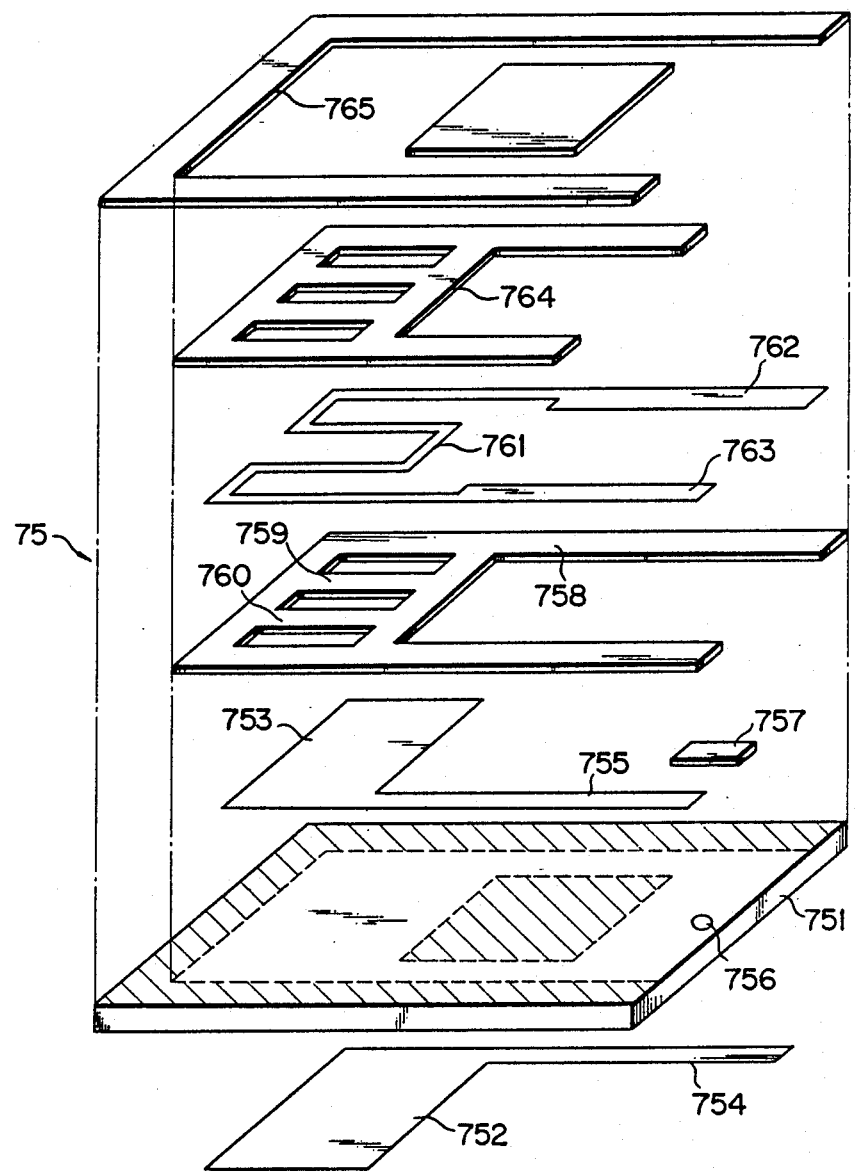
FIG. 15 is an exploded view of a sensor element portion in the above embodiment.

FIG. 15 is an exploded view of oxygen concentration sensor element 75. Plate-like solid-state electrolyte layer 751 surrounds the outer surface of core 75. First and second electrode layers 752 and 753 are respectively formed on both surfaces of electrolyte layer 751 in the range where groove 741 is present at the position of opening 14. Wiring layers 754 and 755 are respectively connected to electrode layers 752 and 753. The distal ends of wiring layers 754 and 755 respectively correspond to positions of grooves 731 and 732 while electrolytic layer 751 is wound around core 75. Wiring layer 755 is guided in groove 732. Wiring layer 754 is connected to wiring layer 757 via through hole 756. Wiring layer 757 is guided in groove 731.

Insulating layer 758 is formed on solid-state electrolyte layer 751. Insulating layer 758 has a window partitioned by bridge members 759 and 760 corresponding to second electrode layer 753. Heater 761 is formed on insulating layer 758 through bridge members 759 and 760. Wiring layers 762 and 763 are connected to heater 761. Insulating layer 764 having the same window as that of insulating layer 758 is formed to cover heater 761 and wiring layers 762 and 763. Heater 761 is insulated from solid-state electrolyte layer 751 by insulating layers 758 and 764. Filling layers 765 and 766 made of the same material as that of solid-state electrolyte layer 751 are formed around laminated insulating layers 758 and 764. The resultant structure is baked to obtain an integral body.

In the third and fourth embodiments, filling layers 663 and 664 and filling layers 765 and 766 are separate members from cores 61 and 71, respectively. However, filling layers have a function for bonding the solid-state electrolyte layers to the cores. Therefore, when the solid-state electrolyte layer is molded, the portions corresponding to the filling layers may be simultaneously molded. The cores, solid-state electrolyte layers and filling layers are made of the same material $ZrO_2$-$Y_2O_3$. However, the material may be selected from $ZrO_2$-$Yb_2O_3$, $ZrO_2$-CaO, $ZrO_2$-MgO and the like. The core and the solid-state electrolyte layer may be formed of $ZrO_2$-$Y_2O_3$, and the filling layers may be formed of $ZrO_2$-$Yb_2O_3$. In this case, diffusion of $Y_2O_3$ and $Yb_2O_3$ occurs, and the resultant materials of the respective components are substantially identical compositions during baking. The solid solubility concentration of $Y_2O_3$ and $Yb_2O_3$ with respect to $ZrO_2$ may be arbitrarily changed.

What is claimed is:

1. A detecting apparatus for detecting the oxygen concentration in an exhaust gas, said apparatus comprising:
    a cylindrical core made of an insulating material and having a hollow portion, said core having a closed distal end and an open proximal end, said proximal end being disposed to introduce a reference gas into the hollow portion, said core further having an opening formed transversely through said core and communicating with the hollow portion of said core;
    a layer made of solid-state electrolyte mounted at least partially around said core so as to close the opening formed in said core, and having first and second electrode layers respectively formed on upper and lower surfaces of said electrolyte layer, said first electrode layer being exposed to a sample gas disposed around an outer surface of said core, and said second electrode layer being exposed to a reference gas introduced into the hollow portion of said core through said opening; and
    an insulating member wound around the outer surface of said core and having a heater with two ends, a pair of conductive layers connected to the ends of the heater and other conductive layers contacting and electrically connected to said first and second electrode layers.

2. An apparatus according to claim 1, wherein said insulating member includes a window, said heater surrounds said window, and said insulating member is wound around the outer surface of said core such that said first electrode layer is exposed to the sample gas through said window.

3. An apparatus according to claim 2, wherein four grooves are formed in the outer surface of the open proximal end of said core, said grooves extending parallel to an axis of said core, and said pair of conductive layers connected to said heater and said other conductive layers connected to said first and second electrode layers being respectively guided in correspondence with said grooves, so that said four grooves constitute terminals.

4. An apparatus according to claim 2, wherein said core and said insulating member constitute an integral body.

5. An apparatus according to claim 1, wherein said solid-state electrolyte layer surrounds half of a circumference of said core and closed said opening, and said insulating member surrounds the remaining half of the circumference of said core.

6. An apparatus according to claim 1, wherein said solid-state electrolyte layer includes first and second electrodes formed on opposite surfaces thereof at a position corresponding to said opening, and is wound around said core so as to surround a circumference of said core and to close said opening, and said insulating member comprises at least one first portion and at least one second portion which are made of an insulating material and located between said core and said solid-state electrolyte layer, thus connecting said solid-state electrolyte layer to the outer surface of said core, and said heater is arranged on said first portion of said insulating member.

7. An apparatus according to claim 6, wherein said core and said solid-state electrolyte layer are made of an oxygen ionic conductor material.

8. An apparatus according to claim 6, wherein said opening extends at least ⅔ of the overall circumferential length of said core, and said insulating member includes bridge members crossing said opening by a line parallel to an axis of said core, said bridge members being adapted to incorporate said heater.

9. An apparatus according to claim 6, wherein said core includes four parallel grooves formed on an outer surface of the open proximal end of said core and extending parallel to an axis of said core, said other conductive layers electrically connected to said first and second electrode layers extending into two of said four parallel grooves, respectively.

10. An apparatus according to claim 1, further comprising a protective layer formed to cover a distal end portion of said core which includes said solid-state electrolyte layer, said protective layer being formed of a porous insulator, so that the sample gas is guided to said first electrode layer on the upper surface of said solid-state electrolyte layer.

* * * * *

UNITED STATES PATENT AND TRADEMARK OFFICE
CERTIFICATE OF CORRECTION

PATENT NO. : 4,908,119

DATED : March 13, 1990

INVENTOR(S) : Toshitaka Saito, Hiromi Sano, Soji Ota and Syohei Udo

It is certified that error appears in the above-identified patent and that said Letters Patent is hereby corrected as shown below:

On the title page:

"(73) Assignee: Nippondenso Co., Ltd., Kariva, Japan" to

--(73) Assignee: Nippondenso Co., Ltd., Kariya, Japan--.

Signed and Sealed this

Fourth Day of June, 1991

*Attest:*

HARRY F. MANBECK, JR.

*Attesting Officer*   *Commissioner of Patents and Trademarks*